US006501005B1

(12) United States Patent
Röber et al.

(10) Patent No.: US 6,501,005 B1
(45) Date of Patent: *Dec. 31, 2002

(54) DNA SEQUENCES WHICH LEAD TO THE FORMATION OF POLYFRUCTANS (LEVANS), PLASMIDS CONTAINING THESE SEQUENCES AS WELL AS A PROCESS FOR PREPARING TRANSGENIC PLANTS

(75) Inventors: Manuela Röber, Berlin; Gebhard Geier, Dossenheim; Klaus Geider, Sandhausen; Lothar Willmitzer, Berlin, all of (DE)

(73) Assignee: Hoechst Schering AgrEvo, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/469,648

(22) Filed: Dec. 22, 1999

Related U.S. Application Data (62) Division of application No. 08/943,374, filed on Oct. 3, 1997, now Pat. No. 6,028,249, which is a division of application No. 08/381,936, filed as application No. PCT/EP93/02110 on Aug. 9, 1993, now Pat. No. 5,792,923.

(30) Foreign Application Priority Data

Aug. 12, 1992 (DE) .......................................... 42 27 061

(51) Int. Cl.$^7$ ............................ A01H 5/00; C12N 5/04; C12N 15/31; C12N 15/52; C12N 15/82
(52) U.S. Cl. ...................... 800/284; 800/288; 800/298; 435/419; 435/430; 435/468
(58) Field of Search .................... 800/278, 284, 800/287, 288; 536/23.7; 435/419, 430, 468

(56) References Cited

U.S. PATENT DOCUMENTS 5,792,923 A * 8/1998 Rober et al. ................ 800/205
5,908,975 A * 6/1999 Caimi et al. ................ 800/298
6,028,249 A * 2/2000 Rober et al. ................ 800/284

FOREIGN PATENT DOCUMENTS

WO          89-12386    * 12/1989

OTHER PUBLICATIONS

Rathsam, C. et al. "The Cell–Bound Fructosyltransferase of *Streptococcus salivarius* : the Carboxyl Terminus Specifies Attachment in a *Streptococcus gordonii* Model System." 1993, Journal of Bacteriology, vol. 175, pp. 4520–4527.*

Giffard, P. M. et al. "The ftf gene encoding the cell–bound fructosyltransferase of *Streptococcus salivarius* ATCC 25975 is preceded by an insertion sequence and followed by FUR1 and clpP homologues." 1993, J. of General Microbiology, vol. 139, pp. 913–920.*

Steinmetz, M. et al. "The DNA sequence of the gene for the secreted *Bacillus subtillis* enzyme levansucrase and its genetic control sites." 1985, Mol Gen Genet, vol. 200, pp. 220–228.*

Tang, L. B. et al. "Isolation and characterization of levansucrase–encoding gene from *Bacillus amyloliquefaciens*." 1990, Gene, vol. 96, pp. 89–93.*

Shiroza, T. and Kuramitsu, H.K. "Sequence Analysis of the *Streptococcus mutans* Fyltransferase Gene and Flanking Regions." 1988, Journal of Bacteriology, vol. 170, pp. 810–816.*

Turk, S. et al. "The vacuolar sorting domain of sporamin transports GUS, but not levansucrase, to the plant vacuole." 1997, New Phytol. , vol. 136, pp. 29–38.*

Rober et al, 1996, Synthesis of fructans in tubers of transgenic starchdeficient potatoplants do not result in increased allocation of carbohydrates. Planta 199:528–536.*

Stryer, 1988. Biochemstry, 3rd ed. W.H. Freeman and Co. (New York) p. 786–787.*

Sonnewald et al, 1991. Transgenic tobacco plants expressing yeast–derived invertase in either the cytosol, vacuole or apoplast: a powerful tool for studying sucrose metabolism and sink/source interactions. Plant J. 1:95–106.*

* cited by examiner

Primary Examiner—David T. Fox
Assistant Examiner—Anne Kubelik
(74) Attorney, Agent, or Firm—Frommer Lawrence & Haug LLP (57) ABSTRACT

DNA which leads to the formation of polyfructans (levans), plasmids containing this DNA, as well as processes using plasmids for preparing transgenic plants with polyfructan (levan) expression.

10 Claims, 3 Drawing Sheets p35S-CW-LEV:

| A | B | C |

Eco RI | Bam HI | Sal I | Sph I
Asp 718 | pBin 19 | Hind III

FIG. 1 p35S-CY-LEV:

| A | B | C |

Eco RI | "Sma I/Bst XI" | Sal I | Sph I
Asp 718 | pBin 19 | Hind III

FIG. 2 p33-CW-LEV:

| A | B | C |

Eco RI | Bam HI | Sal I | Sph I
Asp 718 | pBin 19 | Hind III

FIG. 5 ns which lead to the formation of polyfructans (levans), plasmids containing these sequences as well as a process for preparing transgenic plants

SEQUENCE LISTING

<160> NUMBER OF SEQ ID NOS: 2

<210> SEQ ID NO 1
<211> LENGTH: 1438
<212> TYPE: DNA
<213> ORGANISM: Erwinia amylovora
<220> FEATURE:
<221> NAME/KEY: CDS
<222> LOCATION: (155)..(1399)
<223> OTHER INFORMATION: note = "Levasucrase"

<400> SEQUENCE: 1

```
ggatccccg ggctgcagcg atcatggtta tttataaggg attgttatgt cctgaaaacc 60
acacaacaga accagagtga tttcaaaaaa taaaaagcta ttaatataca gaccttcagc 120
aagaaggtat tcgaaataac ctgtgaggat attt atg tca gat tat aat tat aaa 175
Met Ser Asp Tyr Asn Tyr Lys
1 5
cca acg ctg tgg act cgt gcc gat gca ttg aaa gtt cat gag gat gac 223
Pro Thr Leu Trp Thr Arg Ala Asp Ala Leu Lys Val His Glu Asp Asp
10 15 20
cca acc aca act caa ccg gtt att gac att gca ttc ccg gta atg agt 271
Pro Thr Thr Thr Gln Pro Val Ile Asp Ile Ala Phe Pro Val Met Ser
25 30 35
gaa gaa gtc ttt att tgg gat acc atg cca ttg cga gac ttc gac gga 319
Glu Glu Val Phe Ile Trp Asp Thr Met Pro Leu Arg Asp Phe Asp Gly
40 45 50 55
gag att atc tct gta aat ggt tgg tgt att att ttt acg cta aca gca 367
Glu Ile Ile Ser Val Asn Gly Trp Cys Ile Ile Phe Thr Leu Thr Ala
60 65 70
gat cgc aac act gat aat ccg caa ttc cag gat gaa aat ggc aat tat 415
Asp Arg Asn Thr Asp Asn Pro Gln Phe Gln Asp Glu Asn Gly Asn Tyr
75 80 85
gat att act cgt gac tgg gaa gac aga cat ggt cgt gcg cgt att tgt 463
Asp Ile Thr Arg Asp Trp Glu Asp Arg His Gly Arg Ala Arg Ile Cys
90 95 100
tat tgg tac tca cgc acc ggt aaa gac tgg att ttt ggc ggt cgg gta 511
Tyr Trp Tyr Ser Arg Thr Gly Lys Asp Trp Ile Phe Gly Gly Arg Val
105 110 115
atg gcc gaa ggt gtc gca ccg acg acg cgt gag tgg gcc gga acc ccg 559
Met Ala Glu Gly Val Ala Pro Thr Thr Arg Glu Trp Ala Gly Thr Pro
120 125 130 135
atc ctt tta aac gat cgg ggc gat att gac ctg tat tat acc tgt gtc 607
Ile Leu Leu Asn Asp Arg Gly Asp Ile Asp Leu Tyr Tyr Thr Cys Val
140 145 150
act ccg ggt gca acc att gcc aaa gtg cgc ggt aaa atc gtc act tcc 655
Thr Pro Gly Ala Thr Ile Ala Lys Val Arg Gly Lys Ile Val Thr Ser
155 160 165
gat caa agt gta agc ctg gaa ggt ttt cag cag gtt aca tca ctt ttc 703
Asp Gln Ser Val Ser Leu Glu Gly Phe Gln Gln Val Thr Ser Leu Phe
170 175 180
tct gct gac ggg act att tac cag acg gaa gag cag aac gct ttc tgg 751
Ser Ala Asp Gly Thr Ile Tyr Gln Thr Glu Glu Gln Asn Ala Phe Trp
185 190 195
aac ttc cgt gac cca agc cca ttc att gac agg aat gat ggc aaa tta 799
Asn Phe Arg Asp Pro Ser Pro Phe Ile Asp Arg Asn Asp Gly Lys Leu
200 205 210 215
tat atg ctg ttt gaa gga aac gtg gcg ggg ccg cgc ggt tcg cac gaa 847
Tyr Met Leu Phe Glu Gly Asn Val Ala Gly Pro Arg Gly Ser His Glu
220 225 230
```

```
att acc cag gct gag atg ggt aat gtg ccg ccg ggt tat gaa gat gtg         895
Ile Thr Gln Ala Glu Met Gly Asn Val Pro Pro Gly Tyr Glu Asp Val
            235                 240                 245 ggt ggc gca aaa tat cag gca ggc tgt gtt ggt ctg gct gtg gcc aaa         943
Gly Gly Ala Lys Tyr Gln Ala Gly Cys Val Gly Leu Ala Val Ala Lys
        250                 255                 260 gac ctg tca gga agt gag tgg caa atc ctg cct ccg ctg atc acc gct         991
Asp Leu Ser Gly Ser Glu Trp Gln Ile Leu Pro Pro Leu Ile Thr Ala
265                 270                 275 gtt ggc gta aac gat cag act gaa cgc cct cat ttt gtc ttc cag gat        1039
Val Gly Val Asn Asp Gln Thr Glu Arg Pro His Phe Val Phe Gln Asp
280                 285                 290                 295 ggt aaa tac tat ctg ttc acc att agc cat aag tac act ttt gcc gat        1087
Gly Lys Tyr Tyr Leu Phe Thr Ile Ser His Lys Tyr Thr Phe Ala Asp
            300                 305                 310 aac ctg acc ggc cct gat gga gtg tat ggc ttt gta agc gat aaa ctt        1135
Asn Leu Thr Gly Pro Asp Gly Val Tyr Gly Phe Val Ser Asp Lys Leu
        315                 320                 325 acc ggc cct tac acg ccg atg aat agc tcc ggg ctg gtg ctg ggc aac        1183
Thr Gly Pro Tyr Thr Pro Met Asn Ser Ser Gly Leu Val Leu Gly Asn
330                 335                 340 ccg tct tca caa cct ttc cag aca tat tca cac tat gtt atg cct aat        1231
Pro Ser Ser Gln Pro Phe Gln Thr Tyr Ser His Tyr Val Met Pro Asn
    345                 350                 355 ggg ctg gtc act tcc ttt att gac agt gtt ccg tgg aaa ggt aag gac        1279
Gly Leu Val Thr Ser Phe Ile Asp Ser Val Pro Trp Lys Gly Lys Asp
360                 365                 370                 375 tat cgc att ggc ggt act gaa gct ccg acc gta aaa att ctg ttg aaa        1327
Tyr Arg Ile Gly Gly Thr Glu Ala Pro Thr Val Lys Ile Leu Leu Lys
            380                 385                 390 ggc gat cgc tca ttt att gtt gat agc ttc gat tat gga tat att ccg        1375
Gly Asp Arg Ser Phe Ile Val Asp Ser Phe Asp Tyr Gly Tyr Ile Pro
        395                 400                 405 gca atg aaa gac att act tta aaa taagtctgtt gtcgatatca agcttatcga       1429
Ala Met Lys Asp Ile Thr Leu Lys
        410             415 taccgtcga                                                              1438
```

<210> SEQ ID NO 2
<211> LENGTH: 415
<212> TYPE: PRT
<213> ORGANISM: Erwinia amylovora

<400> SEQUENCE: 2

```
Met Ser Asp Tyr Asn Tyr Lys Pro Thr Leu Trp Thr Arg Ala Asp Ala
1               5                   10                  15

Leu Lys Val His Glu Asp Asp Pro Thr Thr Thr Gln Pro Val Ile Asp
            20                  25                  30

Ile Ala Phe Pro Val Met Ser Glu Glu Val Phe Ile Trp Asp Thr Met
        35                  40                  45

Pro Leu Arg Asp Phe Asp Gly Glu Ile Ile Ser Val Asn Gly Trp Cys
    50                  55                  60

Ile Ile Phe Thr Leu Thr Ala Asp Arg Asn Thr Asp Asn Pro Gln Phe
65                  70                  75                  80

Gln Asp Glu Asn Gly Asn Tyr Asp Ile Thr Arg Asp Trp Glu Asp Arg
                85                  90                  95

His Gly Arg Ala Arg Ile Cys Tyr Trp Tyr Ser Arg Thr Gly Lys Asp
            100                 105                 110
```

-continued

```
Trp Ile Phe Gly Gly Arg Val Met Ala Glu Gly Val Ala Pro Thr Thr
        115                 120                 125

Arg Glu Trp Ala Gly Thr Pro Ile Leu Leu Asn Asp Arg Gly Asp Ile
    130                 135                 140

Asp Leu Tyr Tyr Thr Cys Val Thr Pro Gly Ala Thr Ile Ala Lys Val
145                 150                 155                 160

Arg Gly Lys Ile Val Thr Ser Asp Gln Ser Val Ser Leu Glu Gly Phe
                165                 170                 175

Gln Gln Val Thr Ser Leu Phe Ser Ala Asp Gly Thr Ile Tyr Gln Thr
            180                 185                 190

Glu Glu Gln Asn Ala Phe Trp Asn Phe Arg Asp Pro Ser Pro Phe Ile
        195                 200                 205

Asp Arg Asn Asp Gly Lys Leu Tyr Met Leu Phe Glu Gly Asn Val Ala
    210                 215                 220

Gly Pro Arg Gly Ser His Glu Ile Thr Gln Ala Glu Met Gly Asn Val
225                 230                 235                 240

Pro Pro Gly Tyr Glu Asp Val Gly Gly Ala Lys Tyr Gln Ala Gly Cys
                245                 250                 255

Val Gly Leu Ala Val Ala Lys Asp Leu Ser Gly Ser Glu Trp Gln Ile
            260                 265                 270

Leu Pro Pro Leu Ile Thr Ala Val Gly Val Asn Asp Gln Thr Glu Arg
        275                 280                 285

Pro His Phe Val Phe Gln Asp Gly Lys Tyr Tyr Leu Phe Thr Ile Ser
    290                 295                 300

His Lys Tyr Thr Phe Ala Asp Asn Leu Thr Gly Pro Asp Gly Val Tyr
305                 310                 315                 320

Gly Phe Val Ser Asp Lys Leu Thr Gly Pro Tyr Thr Pro Met Asn Ser
                325                 330                 335

Ser Gly Leu Val Leu Gly Asn Pro Ser Ser Gln Pro Phe Gln Thr Tyr
            340                 345                 350

Ser His Tyr Val Met Pro Asn Gly Leu Val Thr Ser Phe Ile Asp Ser
    355                 360                 365

Val Pro Trp Lys Gly Lys Asp Tyr Arg Ile Gly Gly Thr Glu Ala Pro
    370                 375                 380

Thr Val Lys Ile Leu Leu Lys Gly Asp Arg Ser Phe Ile Val Asp Ser
385                 390                 395                 400

Phe Asp Tyr Gly Tyr Ile Pro Ala Met Lys Asp Ile Thr Leu Lys
                405                 410                 415
```

DNA SEQUENCES WHICH LEAD TO THE FORMATION OF POLYFRUCTANS (LEVANS), PLASMIDS CONTAINING THESE SEQUENCES AS WELL AS A PROCESS FOR PREPARING TRANSGENIC PLANTS

This application is a divisional of prior allowed application Ser. No. 08/943,374, filed Oct. 3, 1997 now U.S. Pat. No. 6,028,249, which in turn is a divisional application of U.S. Ser. No. 08/381,936, filed Feb. 9, 1995 now U.S. Pat. No. 5,792,923, as the National Phase of PCT/EP93/02110, filed Aug. 9, 1993, designating the U.S., published as WO 94/04692, claiming priority from German application P 42 27 061.8, filed Aug. 12, 1992; now U.S. Pat. No. 5,792,923.

FIELD OF THE INVENTION

The present invention relates to DNA sequences which lead to the formation of polyfructans (levans), as well as a process for preparing transgenic plants using plasmids on which these DNA sequences are located.

High molecular weight, water soluble, linear polymers, for example those based on polyacrylates or polymethacrylates, are products of mineral oils and have many important uses. In particular their properties in increasing the viscosity of aqueous systems, in suspending or sedimentation acceleration and complexing are especially valuable from the technical viewpoint. These products are also used in exceptionally large amounts in super absorbers for water binding and in water dilutable lacquers. In spite of the outstanding positive properties, because such products are difficult to dispose of, their use is increasingly coming under criticism because they are not biodegradable.

Alternatives based on recyclable raw materials, especially starches and cellulose, because of the macromolecular structure of these polysaccharides, have been shown to have limited value. As a replacement for non-biodegradable chemically derived polymers, a number of derivatised high polymeric polysaccharides have been considered. Until now, such polysaccharides could only be obtained biotechnologically via suitable fermentation and transglycosidation processes. The products obtained in this way, such as dextrans and polyfructans (levans) are not competitive as raw materials for mass production.

Polyfructans are found in a number of monocotyledonous and dicotyledonous higher plants, in green algae as well as in a number of gram positive and gram negative bacteria (Meier and Reid, (1982) Encyclopedia of Plant Physiology, New Series, 13A 418–471). The role of fructans for the plant development and plant growth is not fully understood. Functions of the fructans that have been proposed are as a protectant against freezing at low temperatures, as alternative carbohydrate stores which limit starch biosynthesis, as well as applied intermediary stores for photoassimilates which are situated in the stems of grasses shortly before their transfer into the seeds.

All fructans contain, as starter molecule for the polymerisation reaction, a molecule of sucrose (glucose-fructose) to which fructose polymers are added.

Depending on the coupling of the fructose molecule, fructans of-plant origin can be classified into four classes (Meier and Reid (1982), Encyclopedia of Plant Physiology, New Series, 13A, 418–471):

a) (2-1) coupled β D-fructans (inulin type)
b) (2-6) coupled β-D-fructans (phlein or levan type)
c) highly branched fructans with a mixture of 2-1 and 2-6 couplings.
d) (2-1) coupled β-D-fructans, which in contrast to the types under a-c, are added completely from fructose residues of polymerisation both from glucose and also from fructose residues from polyfructose residues (neokestose type).

Fructans of bacterial origin correspond either to the levan or to the inulin type (Carlsson (1970) Caries Research 4, 97–113) and Dedonder (1966) Methods Enzymology 8, 500–505).

Experiments on the biosynthesis of fructans in plants and bacteria lead one to conclude that the biosynthesis proceeds by various routes. Bacterial and plant fructans are further distinguished, not particularly in their primary structure but mainly in their molecular weight. Thus, fructans isolated from plants have been shown to have molecular weights of between 5000 and 50,000 d (Pollock and Chatterton (1988) in: The Biochemistry of Plants 14, 109–140), while fructans isolated from bacteria, molecular weights of up to 2,000,000 d have been described (Clarke et al (1991) in: Carbohydrates as Organic Raw Materials, VCH Weinheim, 169–182).

Various microorganisms from the group of Bacillus spp as well as Streptococcus spp produce polyfructoses in which both fructans of the levan type and fructans of the inulin type have been described (Carlsson (1 970) Caries Research 4, 97–113 and Dedonder (1966) Methods Enzymology 8, 500–505).

Experiments on biosynthesis pathways have made it clear that, in comparison to biosynthesis pathways in higher plants, there is a simpler pattern and a sharing of only one enzyme. This enzyme with the trivial name levan sucrase is a transfructosylase (sucrose:.β-D-fructosyl transferase, E.C.2.4.1.10.), which catalyzes the following reaction:

sucrose+acceptor⇒glucose+fructosyl acceptor

Representative acceptors are water, alcohol, sugar or polyfructoses. The hypothesis that only one enzyme catalyses this reaction, depends on the one hand on the examination of the protein chemically purified enzyme, and on the other, to the fact that the gene for levan sucrase has been isolated from various Bacillus spp. as well as from a Streptococcus spp. and after transfer into E. coli leads to the formation of levan in E. coli (Gay et al (1983) J. Bacteriology 153, 1424–1431 and Sato et al. (1986) Infection and Immunity 52, 166–170).

Until now, genes for levan sucrase from Bacillus amyloliquefaciens (Tang et al. (1990) Gene 96, 89–93) and Bacillus subtilis (Steinmetz et al. (1985) Mol. Gen. Genetics 200, 220–228), have been described, and demonstrate relatively high homology with each other and both of which catalyze the synthesis of fructans of the levan type. Further, a fructosyl transferase from Streptococcus mutans (Shiroza et al. (1988) J. Bacteriology 170, 810–816) has been described. This shows little homology to either levan sucrases from Bacillus spp.. The fructan formed in Streptococcus mutans is of the inulin type.

In WO 89/12386, there is described the possibility of producing carbohydrate polymers such as dextran or levan in transgenic plants, especially in the fruit of transgenic plants. To prepare these plants, the use of levan sucrases from Aerobacter levanicum, Streptococcus salivarius and Bacillus subtilis and the use of dextran sucrases from Leuconostoc mesenteroides have been described.

Further, the construction of chimeric genes is described which may be suitable for the expression of the levan sucrase from Bacillus subtilis as well as the dextran sucrase fom Leuconostoc mesenteroides in transgenic plants. Also described is the preparation of transgenic plants containing these constructs. Further, the preparation of transgenic plants that contain these constructs are described. Whether polyfructans can actually be produced by the described process is not known.

There is also described a series of processes for modifying the carbohydrate concentration and/or concentrating carbohydrates in transgenic plants by means of biotechnological methods. Thus, in view of the fact that increasing of the starch concentration and the modification of the starch in physical and chemical respects is already known, then a modification of the carbohydrate content of potato plants by raising or lowering the ADP-glucose-pyrophosphorylase activity can be achieved (EP 455 316).

From EP 442 592 it is further known that a modification of the distribution of photoassimilates by means of cytosolic and apoplastic invertase is possible and that the yield as well as the drought and frost resistance of potato plants can be modified through the expression of a heterologous pyrophosphatase gene in potato plants.

In order to adapt the physico-chemical parameters of raw materials which are increasingly being used, such as polysaccharides, to the requirements of the chemical industry, as well as to minimize the costs of obtaining these products, processes for the preparation of transgenic plants have to be developed which lead in comparison with known processes to better, higher yielding plants.

SUMMARY OF THE INVENTION

It has now been surprisingly found that the DNA sequence of the levan sucrase from a gram-negative bacterium of the species Erwinia amylovora with the nucleotide sequence (Seq-ID NO 1):

```
GGATCCCCCG GGCTGCAGCG ATCATGGTTA TTTATAAGGG ATTGTTATGT          50

CCTGAAAACC ACACAACAGA ACCAGAGTGA TTTCAAAAAA TAAAAAGCTA         100

TTAATATACA GACCTTCAGC AAGAAGGTAT TCGAAATAAC CTGTGAGGAT       150

ATTT ATG TCA GAT

Met Ser Asp

TAT AAT TAT AAA CCA ACG CTG TGG ACT CGT GCC GAT GCA TTG AAA   163

Tyr Asn Tyr Lys Pro Thr Leu Trp Thr Arg Ala Asp Ala Leu Lys 5                  10                  15
GTT CAT GAG GAT GAC CCA ACC ACA ACT CAA CCG GTT ATT GAC ATT   253
Val His Glu Asp Asp Pro Thr Thr Thr Gln Pro Val Ile Asp Ile 20                  25                  30
GCA TTC CCG GTA ATG AGT GAA GAA GTC TTT ATT TGG GAT ACC ATG   298
Ala Phe Pro Val Met Ser Glu Glu Val Phe Ile Trp Asp Thr Met 35                  40                  45
CCA TTG CGA GAC TTC GAC GGA GAG ATT ATC TCT GTA AAT GGT TGG   333
Pro Leu Arg Asp Phe Asp Gly Glu Ile Ile Ser Val Asn Gly Trp 50                  55                  60
TGT ATT ATT TTT ACG CTA ACA GCA GAT CGC AAC ACT GAT AAT CCG   388
Cys Ile Ile Phe Thr Leu Thr Ala Asp Arg Asn Thr Asp Asn Pro 65                  70                  75
CAA TTC CAG GAT GAA AAT GGC AAT TAT GAT ATT ACT CGT GAC TGG   433
Gln Phe Gln Asp Glu Asn Gly Asn Tyr Asp Ile Thr Arg Asp Trp 80                  85                  90
GAA GAC AGA CAT GGT CGT GCG CGT ATT TGT TAT TGG TAC TCA CGC   478
Glu Asp Arg His Gly Arg Ala Arg Ile Cys Tyr Trp Tyr Ser Arg 95             100                 105
ACC GGT AAA GAC TGG ATT TTT GGC GGT CGG GTA ATG GCC GAA GGT   523
Thr Gly Lys Asp Trp Ile Phe Gly Gly Arg Val Met Ala Glu Gly 110                 115                 120
GTC GCA CCG ACG ACG CGT GAG TGG GCC GGA ACC CCG ATC CTT TTA   568
Val Ala Pro Thr Thr Arg Glu Trp Ala Gly Thr Pro Ile Leu Leu 125                 130                135
AAC GAT CGG GGC GAT ATT GAC CTG TAT TAT ACC TGT GTC ACT CCG   613
Asn Asp Arg Gly Asp Ile Asp Leu Tyr Tyr Thr Val Cys Thr Pro 140                 145                     150
GGT GCA ACC ATT GCC AAA GTG CGC GGT AAA ATC GTC ACT TCC GAT   658
Gly Ala Thr Ile Ala Lys Val Arg Gly Lys Ile Val Thr Ser Asp 155                 160                 165
CAA AGT GTA AGC CTG GAA GGT TTT CAG CAG GTT ACA TCA CTT TTC   703
Gln Ser Val Ser Leu Glu Gly Phe Gln Gln Val Thr Ser Leu Phe
```

```
          170               175               180
TCT GCT GAC GGG ACT ATT TAC CAG ACG GAA GAG CAG AAC GCT TTC      748
Ser Ala Asp Gly Thr Ile Tyr Gln Thr Glu Glu Gln Asn Ala Phe 185               190               195
TGG AAC TTC CGT GAC CCA AGC CCA TTC ATT GAC AGG AAT GAT GGC      793
Trp Asn Phe Arg Asp Pro Ser Pro Phe Ile Asp Arg Asn Asp Gly 200               205               210
AAA TTA TAT ATG CTG TTT GAA GGA AAC GTG GCG GGG CCG CGC GGT      838
Lys Leu Tyr Met Leu Phe Glu Gly Asn Val Ala Gly Pro Arg Gly 215               220               225
TCG CAC GAA ATT ACC CAG GCT GAG ATG GGT AAT GTG CCG CCG GGT      883
Ser His Glu Ile Thr Gln Ala Glu Met Gly Asn Val Pro Pro Gly 230               235               240
TAT GAA GAT GTG GGT GGC GCA AAA TAT CAG GCA GGC TGT GTT GGT      928
Tyr Glu Asp Val Gly Gly Ala Lys Tyr Gln Ala Gly Cys Val Gly 245               250               255
CTG GCT GTG GCC AAA GAC CTG TCA GGC AGT GAG TGG CAA ATC CTG      973
Leu Ala Val Ala Lys Asp Leu Ser Gly Ser Glu Trp Gln Ile Leu 260               265               270
CCT CCG CTG ATC ACC GCT GTT GGC GTA AAC GAT CAG ACT GAA CGC     1018
Pro Pro Leu Ile Thr Ala Val Gly Val Asn Asp Gln Thr Glu Arg 275               280               285
CCT CAT TTT GTC TTC CAG GAT GGT AAA TAC TAT CTG TTC ACC ATT     1063
Pro His Phe Val Phe Gln Asp Gly Lys Tyr Tyr Leu Phe Thr Ile 290               295               300
AGC CAT AAG TAC ACT TTT GCC GAT AAC CTG ACC GGC CCT GAT GGA     1108
Ser His Lys Tyr Thr Phe Ala Asp Asn Leu Thr Gly Pro Asp Gly 305               310               315
GTG TAT GGC TTT GTA AGC GAT AAA CTT ACC GGC CCT TAC ACG CCG     1153
Val Tyr Gly Phe Val Ser Asp Lys Leu Thr Gly Pro Tyr Thr Pro 320               325               330
ATG AAT AGC TCC GGG CTG GTG CTG GGC AAC CCG TCT TCA CAA CCT     1198
Met Asn Ser Ser Gly Leu Val Leu Gly Asn Pro Ser Ser Gln Pro 335               340               345
TTC CAG ACA TAT TCA CAC TAT GTT ATG CCT AAT GGG CTG GTC ACT     1243
Phe Gln Thr Tyr Ser His Tyr Val Met Pro Asn Gly Leu Val Thr 350               355               360
TCC TTT ATT GAC AGT GTT CCG TGG AAA GGT AAG GAC TAT CGC ATT     1288
Ser Phe Ile Asp Ser Val Pro Trp Lys Gly Lys Asp Tyr Arg Ile 365               370               375
GGC GGT ACT GAA GCT CCG ACC GTA AAA ATT CTG TTG AAA GGC GAT     1333
Gly Gly Thr Glu Ala Pro Thr Val Lys Ile Leu Leu Lys Gly Asp 380               385               390
CGC TCA TTT ATT GTT GAT AGC TTC GAT TAT GGA TAT ATT CCG GCA     1378
Arg Ser Phe Ile Val Asp Ser Phe Asp Tyr Gly Tyr Ile Pro Ala 395               400           405
ATG AAA GAC ATT ACT TTA AAA TAAGTCTGTT GTCGATATCA AGCTTATCGA    1429
Met Lys Asp Ile Thr Leu Lys 410               415
TACCGTCGA
``` makes possible the preparation of large amounts of polyfructans (levans) in transgenic plants, which decisively meet the needs of the chemical industry in respect of recyclable raw materials.

By integration of a DNA sequence in a plant genome, on which the above given DNA sequence is located, the polyfructan (levan) expression in plants, especially in leaves and tubers is made possible. The levan sucrase of the invention shows, at the DNA level, no significant homology to the known levan sucrases.

The invention further provides a process for the preparation of transgenic plants with polyfructan (levan) expression in leaves and tubers that comprises the following steps:

(a) preparation of a DNA sequence with the following partial sequences:

i) a promoter which is active in plants and ensures formation of an RNA in the intended target tissues or target cells, ii) a DNA sequence of a levan sucrase, and iii) a 3'-non-translated sequence, which in plant cells leads to the termination of the transcription as well as the addition of poly A residues to the 3'-end of the RNA,
(b) transfer and integration of the DNA sequence in the plant genome of a recombinant double stranded DNA molecule from plant cells using a plasmid, and
(c) regeneration of intact whole plants from the transformed plant cells.

The levan sucrase obtained in process step (a,) ii) preferably shows the nucleotide sequence noted under sequence ID No 1.

The levan sucrase catalyses the following reaction:

$$\text{Sucrose-(fructose)}_n + \text{sucrose} \Rightarrow \text{sucrose-(fructose)}_{n+1} + \text{glucose}.$$

Using this process in principle, all plants can be modified in respect to a polyfructan (levan) expression, preferably crops such as maize, rice, wheat, barley, sugar beet, sugar cane, tobacco and potatoes.

In process step (b), in principle, all plasmids can be used which have the DNA sequence given under sequence ID No 1. Preferably used are plasmid p35s-CW-LEV (DS3.M) 7186), plasmid P35s-CY-LEV (DSM 7187) or plasmid P33-CW-LEV (DSM 7188).

Since sucrose represents the substrate for the levan sucrase, the production of polyfructans is especially advantageous in those organs that store large amounts of sucrose. Such organs are for example, the roots of sugar beet or the stems of sugar cane. It is especially useful in genetically modified potatoes, which store sucrose in their tubers, through the blocking of starch biosynthesis.

Biosynthesis of sucrose takes place in the cytosol, while in contrast, storage is in the vacuole. During transport into the storage tissues of a sugar beet or potato or into the endosperm of seeds, the sucrose must cross the intercellular space. In the production of polyfructans, all three cell compartments are suitable, i.e. cytosol, vacuole and intercellular space.

The coding sequence of the levan sucrase of the nucleotide sequence ID No 1 can be provided with a promoter that ensures the transcription occurs in a specified order and which is coupled in sense orientation (3'-end of the promoter to the 5'-end of the coding sequence) on to the coding sequence which codes for the enzyme to be formed. The termination signal, which determines the termination of the mRNA synthesis, is adhered to the 3'-end of the coding sequence. In order to direct the enzyme which is expressed in specified sub-cellular compartments such as chloroplasts, amyloplasts, mitochondria, vacuoles, cytosol or intercellular space, a so-called signal sequence or a transit peptide coding sequence can be positioned between the promoter and the coding sequence. This sequence must be in the same reading frame as the coding sequence of the enzyme.

For the introduction of the DNA sequence of the invention in higher plants, a large number of cloning vectors are available which contain a replication signal for *E. coli* and a marker which allows a selection of the transformed cells. Examples of vectors are pBR 322, pUC-series, M13 mp-series, pACYC 184; EMBL 3 etc.. According to the introduction method of the desired gene in the plant, other DNA sequences may be suitable. Should the Ti-or Ri-plasmid be used, e.g. for the transformation of the plant cell, then at least the right boundary, often however both the right and left boundaries of the Ti-and Ri-Plasmid T-DNA, is attached, as a flanking region, to the gene being introduced. The use of T-DNA for the transformation of plants cells has been intensively researched and is well described in EP 120 516; Hoekama, In: The Binary Plant Vector System, Offset-drukkerij Kanters B.V. Alblasserdam, (1985), Chapter V; Fraley, et al., Crit. Rev. Plant Sci., 4:1–46 and An et al. (1 985) EMBO J. 4: 277–287. Once the introduced DNA is integrated in the genome, it is as a rule stable there and remains also in the offspring of the original transformed cells. It normally contains a selection marker, which induces resistance in the transformed plant cells against a biocide or antibiotic such as kanamycin, G 418, bleomycin, hygromycin or phosphinotricin etc. The individual marker employed should therefore allow the selection of transformed cells from cells that lack the introduced DNA.

For the introduction of DNA into a plant, besides transformation using Agrobacteria, there are many other techniques available. These techniques include the fusion of protoplasts, microinjection of DNA and electroporation, as well as ballistic methods and virus infection. From the transformed plant material, whole plants can be regenerated in a suitable medium that contains antibiotics or biocides for the selection. The resulting plants can then be tested for the presence of introduced DNA. No special demands are placed on the plasmids in injection and electroporation. Simple plasmids, such as e.g. pUC-derivatives can be used. Should however whole plants be regenerated from such transformed cells the presence of a selectable marker gene is necessary. The transformed cells grow within the plants in the usual manner (see also McCormick et al. (1986) Plant Cell Reports 5: 81–84). These plants can be grown normally and crossed with plants that possess the same transformed genes or different. The resulting hybrid individuals have the corresponding phenotypical properties.

Deposits

The following plasmids were deposited at the Deutschen Sammlung von Mikroorganismen (DSM) in Braunschweig, Germany on the 16.07.1992 (deposit number):

Plasmid p35s-CW-LEV (DSM 7186)

Plasmid p35s-CY-LEV (DSM 7187)

Plasmid p33-CW-LEV (DSM 7188)

DESCRIPTION OF THE FIGURES

Fru=fructose, Suc=sucrose, Kes=kestose c1=control 1, c2=control 2, M=marker

DETAILED DESCRIPTION OF THE INVENTION

In order to understand the examples forming the basis of this invention all the processes necessary for these tests and which are known per se will first of all be listed:

1. Cloning Process

The vector pUC 18 (Yanisch-Perron et al. (1985) Gene 33:103–119) was used for cloning.

For the plant transformations, the gene constructs were cloned in the binary vector BIN 19 (Bevan (1984) Nucl. Acids Res 12: 8711–8720)

2. Bacterial Strains

The *E. coil* strain BMH71-18 (Messing et al., Proc. Natl. Acad. Sci. U.S.A. (1977), 24, 6342–6346) or TB1 was used for the pUC vectors. TB1 is a recombinant-negative, tetracycline-resistant derivative of strain JM101 (Yanisch-Perron et al., Gene (1985), 33, 103–119). The genotype of the TB1 strain is (Bart Barrel, personal communication): F' (traD36, proAB, lacI, lacZ.ΔM15), Δ(lac, pro), SupE, thiS, recA, Sr1::Tn10(TcR).

The transformation of the plasmids into the potato plants was carried out using *Agrobacteria tumefaciens* strain LBA4404 (Bevan, (1984), Nuci. Acids Res. 12, 8711–8720).

3. Transformation of *Agrobacterium tumefaciens*

In the case of BIN19 derivatives, the insertion of the DNA into the Agrobacteria was effected by direct transformation in accordance with the method of Holsters et al., (1978) (Mol Gene Genet 163:181–187). The plasmid DNA of the transformed Agrobacteria was isolated in accordance with the method of Birnboim and Doly (1979) (Nucl Acids Res 7:1513–1523) and was analyzed by gel electrophoresis after suitable restriction cleavage.

4. Plant Transformation

A) Tobacco: 10 ml of an overnight culture of *Agrobacteria tumefaciens*, grown under selection, was centrifuged off, the supernatant was discarded, and the bacteria were re-suspended in the same volume of antibiotic-free medium. In a sterile petri dish, leaf discs of sterile plants (approximately 1 cm$^2$), the central vein of which had been removed, were immersed in this bacterial suspension. The leaf discs were then placed in a closely packed arrangement in petri dishes containing MS medium (Murashige et al. (1962) Physiologia Plantarum 15, 473–497) with 2% sucrose and 0.8% bacto agar. After two days incubation in the dark at 25° C., they were transferred onto MS medium containing 100 mg/l kanamycin, 500 mg/l claforan, 1 mg/l benzylaminopurine (BAP), 0.2 mg/l of naphthylacetic acid (NAA) and 0.8% bacto agar. Growing shoots were transferred onto hormone-free MS medium with 250 mg/l of claforan.

B) Potato: Ten small leaves, wounded with a scalpel, of a sterile potato culture were placed in 10 ml of MS medium with 2% sucrose containing 30–50μl of an *Agrobacteria tumefaciens* overnight culture grown under selection. After 3–5 minutes gentle shaking, the leaves were laid out on MS medium of 1.6% glucose, 2 mg/l of zeatin ribose, 0.02 mg/l of naphthylacetic acid, 0.02 mg/l of gibberellic acid, 500 mg/l of claforan, 50 mg/l of kanamycin and 0.8% bacto agar. After incubation for one week at 25° C. and 3000 lux, the claforan concentration in the medium was reduced by half. Further cultivation was carried out using the method described by Rocha-Sosa et al. (1989) EMBO Journal 8, 29).

5. Analysis of Genomic DNA from Transgenic Plants

The isolation of genomic plant DNA was carried out according to Rogers et al. (1985) Plant Mol Biol 5, 69–76).

For the DNA analysis, after suitable restriction cleavage, 10 to 20 μg of DNA were analyzed, by means of Southern blotting, for the integration of the DNA sequences to be investigated.

6. Analysis of the total RNA from Transqenic Plants

The isolation of plant total RNA was carried out according to Logemann et al. (1987), Analytical Biochem. 163, 16–20.

For the analysis, 50 μg portions of total RNA were investigated, by means of Northern blotting, for the presence of the transcripts sought.

7. Extraction and Determination of Polyfructose in Plants

The extraction and determination were carried out according to the method of Portis H. G. (1990), Meth. Plant Biochem. 2, 353–369.

EXAMPLE 1

Figure 1:
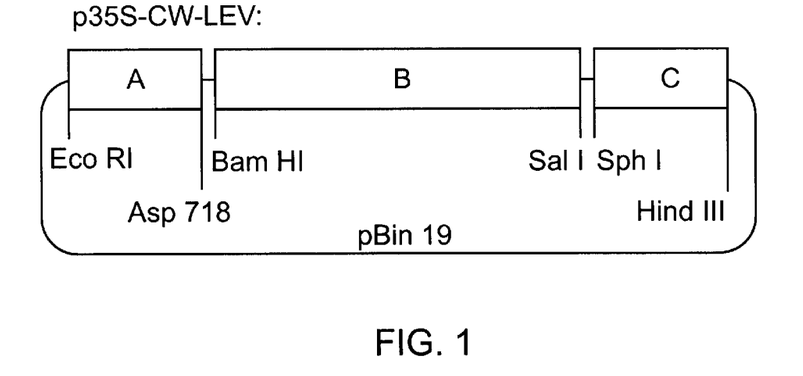
FIG. 1 shows the structure of the p35-CW-LEV plasmid. It comprises the three fragments A, B and C. Fragment A contains the 35s promoter of the cauliflower mosaic virus (CaMV), nucleotides 6906–7437. Fragment B contains the sequence of the nucleotides 689–2122 of the levan sucrase from *Erwinia amylovora* (Seq. ID No. 1). Fragment C contains the polyadenylation signal of the gene 3 of the T-DNA of the Ti-plasmid, pTi ACH 5, nucleotides 11749–11939.

Preparation of Plasmid p35s-CW-LEV and Insertion of the Plasmid Into the genome of Tobacco and Potato The plasmid p35s-CW-LEV comprises the three fragments A, B and C, which were cloned in the cutting sites for restriction enzymes of the polylinker from pUC 18 (see FIG. 1).

Fragment A contains the 35S promoter of cauliflower mosaic virus (CaMV). It contains a fragment that includes the nucleotides 6909 to 7437 of CaMV (Franck et al. (1980) Cell 21, 285–294) and was isolated as Eco RI-Kpn I fragment from plasmid pDH 51 (Pietrzak et al., Nucleic Acids Research 14, 5857–5868) and cloned between the Eco RI-Kpn I cutting sites of the polylinker of plasmid pUC 18.

Fragment B contains the sequence of the nucleotides 689–2122 of the gene of the levan sucrase from *Erwinia amylovora* (Seq. ID No.1) and was cloned between the BamHI/SalI cutting positions of the polylinker of pUC 18.

Fragment C contains the polyadenylation signal of the gene 3 of the T-DNA of the Ti-plasmid, pTi ACH 5 (Gielen et al (1984); EMBO J. 3, 835–846) nucleotides 11749–11939 which was isolated as Pvu II-Hind III fragment from the plasmid pAGV 40 (Herrera-Estrella et al (1983) Nature 303, 209–213) and, after addition of Sph I linkers to the Pvu II cutting positions, was cloned between the Sphl-Hind III cutting positions of the polylinker of pUC 18.von pUC 18. The plasmid p35s-CW-LEV has a size of 2151 bp.

Figure 4:
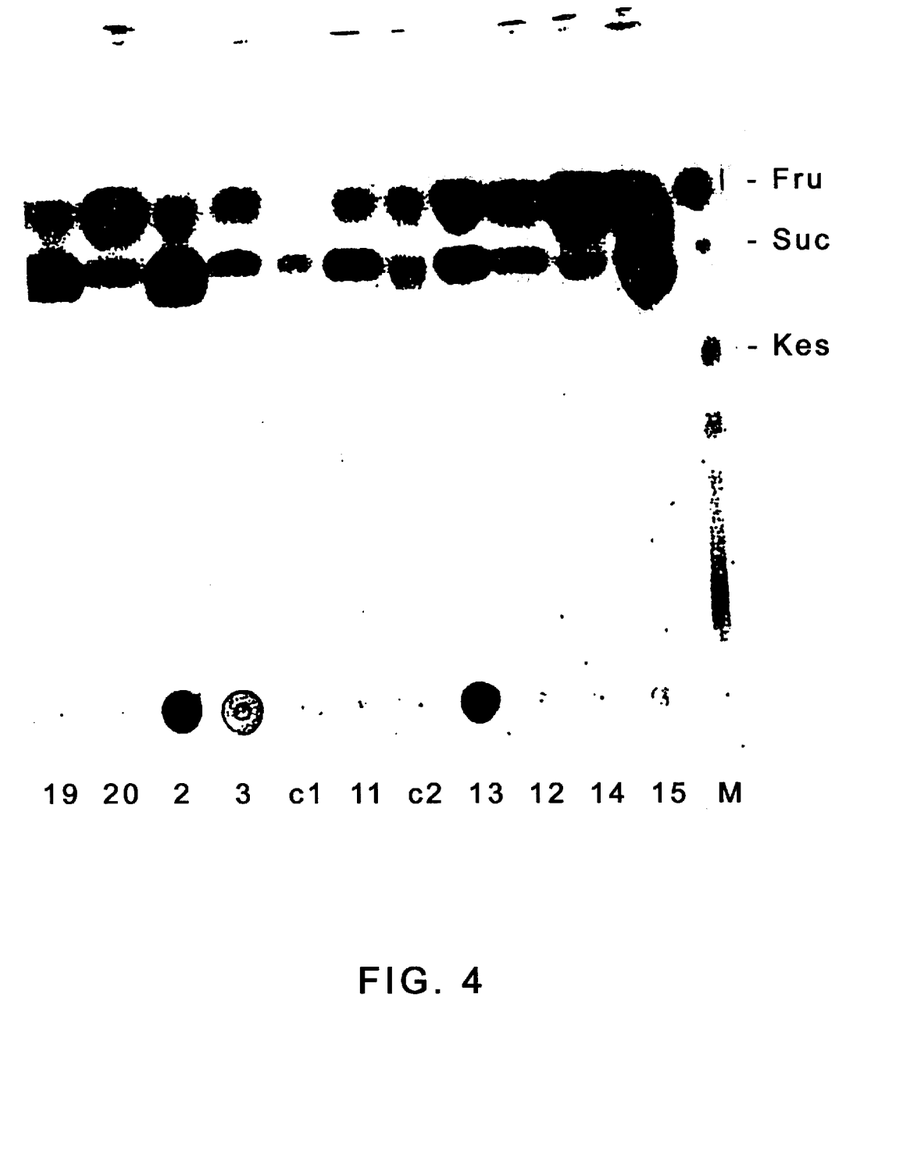
FIG. 4 shows the detection of polyfructan in transformed tobacco plants (No. 2, 3 and 13). In this.

The part of the plasmid p35s-CW-LEV comprising the fragments A, B and C was introduced in binary vectors and using the Agrobacteria system was introduced into tobacco and potato plants. Intact plants were regenerated from transformed cells. The analysis of the leaves from a series of Tobacco plants transformed with this gene, clearly showed the presence of polyfructan (levan) which is traced back to the expression of the gene 35s-Cw-LEV (see FIG. 4).

EXAMPLE 2

Preparation of Plasmid p35s-CY-LEV and Insertion of the Plasmid Into the Genome of Tobacco and Potato This Example was carried out in an analogous manner to that described under Example 1, but with the modification, that the Fragment B (coding for the levan sucrase) is shortened on the nucleotide at the 5'-end. This results in the expression of the protein in the cytosol of transgenic plants.

Figure 2:
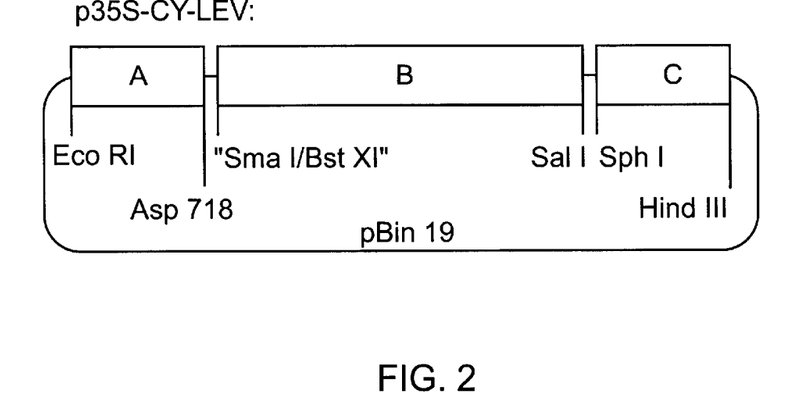
FIG. 2 shows the structure of the p35s-CY-LEV plasmid. It comprises the three fragments A, B and C. Fragment A contains the 35s promoter of the cauliflower mosaic virus (CaMV), nucleotides 6909–7437.Fragment B contains the sequence of the nucleotides 864–2122 of the levan sucrase from *Erwinia amylovora* (Seq. ID No.1). Fragment C contains the polyadenylation signal of the gene 3 of the T-DNA of the Ti-plasmid, pTi ACH 5.

The plasmid p35s-CY-LEV comprises the three fragments A, B and C, which were cloned in the cutting sites for restriction enzymes of the polylinker from pUC 18 (see FIG. 2).

Fragment A contains the 35S promoter of cauliflower mosaic virus (CaMV). It contains a fragment that includes the nucleotides 6909 to 7437 of CaMV (Franck et al. (1980) Cell 21, 285–294) and was isolated as Eco RI-Kpn I fragment from plasmid pDH 51 (Pietrzak et al., Nucleic Acids Research 14, 5857–5868) and cloned between the-Eco RI-Kpn I cutting sites of the polylinker of plasmid pUc 18.

Fragment B contains the sequence of the nucleotides 864–2122 of the gene of the levan sucrase from *Erwinia amylovora* (Seq. ID No.1) and was cloned between the SmaI/SalI cutting positions of the polylinker of pUC 18.

Fragment C contains the polyadenylation signal of the gene 3 of the T- DNA of the Ti-plasmid, pTi ACH 5 (Gielen et al (1984); EMBO J. 3, 835–846) nucleotides 11749–11939 which was insolated as Pvu II-Hind III fragment from the plasmid pAGV 40 (Herrera-Estrella et al (1983) Nature 303, 209–213) and, after addition of Sph I linkers to the Pvu II cutting positions, was cloned between the SphI-Hind III cutting positions of the polylinker of pUC 18.von pUC 18. The plasmid p35s-CY-LEV has a size of 1976 bp.

The part of the plasmid p35s-CY-LEV comprising the fragments A, B and C was introduced in binary vectors and using the Agrobacteria system was introduced into tobacco and potato plants. Intact plants were regenerated from transformed cells.

EXAMPLE 3

Figure 3:
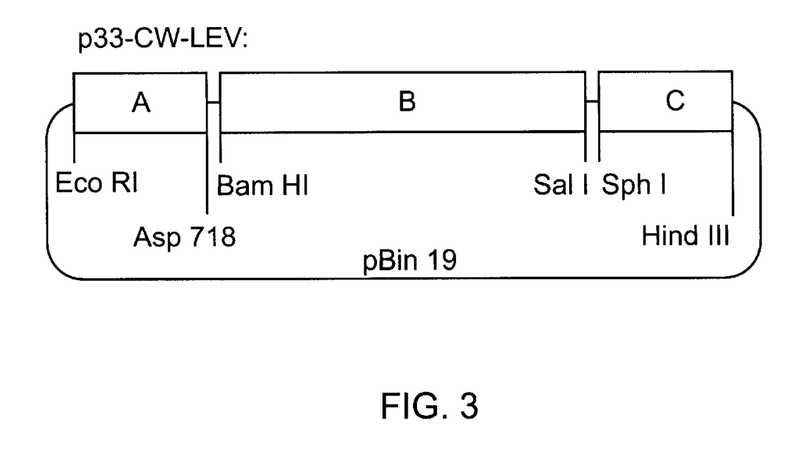
FIG. 3 shows the structure of the p33-CW-LEV plasmid. It comprises the three fragments A, B and C. Fragment A contains the DraI-DraI-fragment (position -1512 to position+14) of the promoter region of the patatin gene B33. Fragment B contains the sequence of the nucleotides 689–2122 of the levan sucrase from *Erwinia amylovora* (Seq. ID No.1). Fragment C contains the polyadenylation signal of the gene 3 of the T-DNA of the Ti-plasmid, pTi ACH 5, nucleotides 11749–11939.

Preparation of Plasmid p35s-CY-LEV and Insertion of the Plasmid Into the Genome of Tobacco and Potato This Example was carried out in an analogous manner to that described under Example 1, but with the 35s promoter being replaced with the promoter of the class I patatin Gene B33 (Rocha-Sosa et al, (1989) EMBO J 8, 23–29) The plasmid p33-CW-LEV comprises the three fragments A, B and C, which were cloned in the cutting sites for restriction enzymes of the polylinker from pUC 18 (see FIG. 3).

Fragment A contains the Dral-Dral fragment (position-1512 to position+14) of the promoter region of the patatin gene B33 (Rocha-Sosa et al (1989) EMBO J. 8, 23–29), which was cloned in the Sma I position of the polylinker of pUC 118.

Fragment B contains the sequence of the nucleotides 689–2122 of the gene of the levan sucrase from *Erwinia amylovora* (Seq. ID No.1) and was cloned between the BamHI/SalI cutting positions of the polylinker of pUC 18.

Fragment C contains the polyadenylation signal of the gene 3 of the T-DNA of the Ti-plasmid, pTi ACH 5 (Gielen et al (1984); EMBO J. 3, 835–846) nucleotides 11749–11939 which was insolated as Pvu II-Hind III fragment from the plasmid pAGV 40 (Herrera-Estrella et al (1983) Nature 303, 209–213) and, after addition of Sph I linkers to the Pvu II cutting positions, was cloned between the SphI-Hind III cutting positions of the polylinker of pUC 18.von pUC 18. The plasmid p33-CW-LEV has a size of 3149 bp.

The part of the plasmid p33-CW-LEV comprising the fragments A, B and C was introduced in binary vectors and using the Agrobacteria system was introduced into tobacco and potato plants. Intact plants were regenerated from transformed cells. The analysis of the leaves from a series of Tobacco plants transformed with this gene, clearly showed the presence of polyfructan (levan) which is traced back to the expression of the gene 33-CW-LEV.

EXAMPLE 4

Analysis of $\beta$2,6-D-Fructofurane (levan) Synthesized in Transgenic Plants by 13C-NMR Spectroscopm The analysis of transgenic plants transformed with the construct p35S-CW-LEV is shown as an example. This analysis can equally be applied to transgenic plants transformed with the constructs p35S-CW-LEV or p35S-CY-LEV.

To obtain sufficient amounts of levan synthesized by transgenic plants to perform NMR spectroscopy, about 10 g of leaf tissue was ground in 10 ml of water. The homogenate is then centrifuged at 4000 Rpm in a Beckman Minifuge and the supernatant is applied to a PD 10 column (LKB-Pharmacia) to remove lower molecular weight compounds. The column had been equilibrated with water before the 2.5 ml of the supernatant was applied and higher molecular weight compounds were then eluted with 3.5 ml of water. The eluate was further purified by adding ion exchange beads (AG 501 X8, Biorad) and shaking for 30 minutes. After centrifugation at 4000 Rpm (Minifuge, Beckman) to remove the beads, the supernatant is applied to a Sepharose 4B column (diameter 16 cm, separating volume 24 ml) to remove the short sugar chains. The eluate is vacuum dried in a vacuum centrifuge (univapo 150 H. Uniquip, Martinsried (FRG)) and then analyzed by 13C-NMR under the following conditions:

| PULPROG | zgdc30 | F2-Processing parameters | |
|---|---|---|---|
| SOLVENT | D20 | SI | 32768 |
| AQ | 1.3762726 sec | SF | 100.5485322 MHz |
| FIDRES | 0.363305 Hz | WDW | EM |
| DW | 21.0 usec | SSB | 0 |
| RG | 32768 | LB | 0.50 Hz |
| NUCLEUS | 13C | GB | 0 |
| D11 | 0300000 sec | PC | 1.40 |
| P31 | 100.0 usec | | |
| S2 | 20 dB | 10 NMR plot parameters | |
| HLT | 1 dB | CX | 33.00 cm |
| D1 | 1.0000000 sec | FTP | 123.000 ppm |
| P1 | 6.5 usec | FT | 12367.47 Hz |
| DE | 26.3 usec | F2P | −6.000 ppm |
| SF01 | 0.5597430 MHz | F2 | −603.29 Hz |
| SWH | 23809.58 Hz | PPMCM | 3.90909 ppm/cm |
| TD | 65536 | HZCM | 393.05334 Hz/cm |
| NS | 8000 | | |
| DS | 2 | | |

Figure 5:
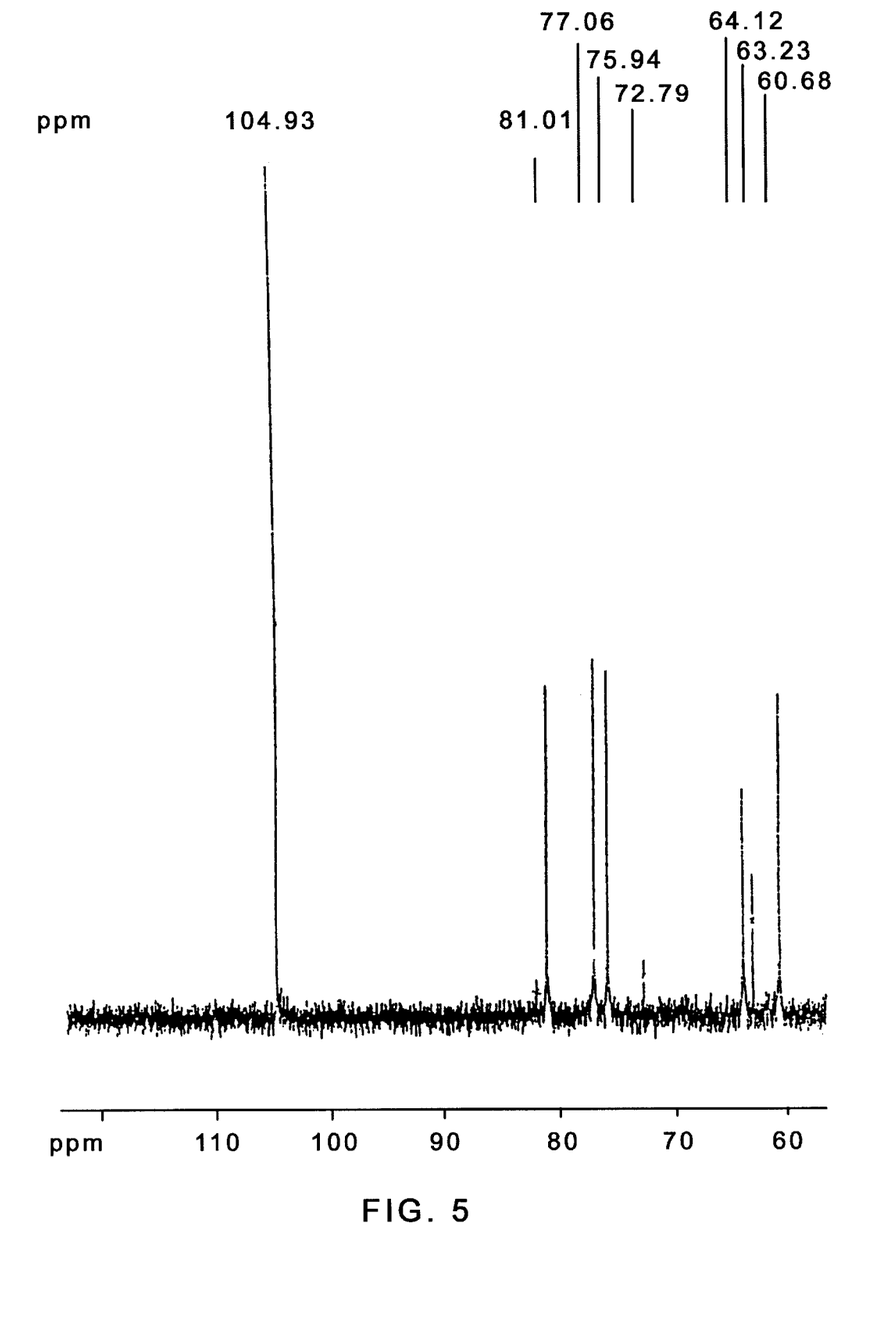
FIG. 5 shows NMR peaks for levan extracted from transformed plants.

The result of the analysis is shown in FIG. 5. The pattern of NMR peaks obtained is the same as it is obtained for levan as published by Gross et al., 1992, Physiol Mol Plant Pathol 40:371.

This proves that the transformed plants synthesize levan after transformation by one of the constructs described in examples 1 to 3.

What is claimed is:

1. A method for producing a transgenic plant with modified polyfructan formation comprising:
   transforming a plant cell so as to contain and express a DNA molecule encoding a bacterial polyctan sucrase wherein polyfructan sacrase expression leads to polyfructan sucrase activity in the vacuoles of the plant; and
   regenerating an intact whole plant from the cell which contains and expresses the DANA molecule.

2. The method of claim 1 wherein the DNA molecule is derived from *Bacillus amyloliquefaciens* or *Streptococcus mutans*.

3. The method of claim 2 wherein the DNA molecule is derived from *Bacillus amyloliquefaciens*.

4. The method of claim 2 wherein the DNA molecule is derived from *Streptococcus mutans*.

5. A method for producing a transgenic plant with modified polyfructan formation comprising:
   transforming a plant cell so as to contain and express a DNA molecule encoding a polyfructan sucrase wherein polyfructan sucrase expression leads to polyfructan sucrase activity in the vacuoles of the plant and wherein the DNA molecule is derived from *Bacillus amyloliquefaciens*; and
   regenerating an intact whole plant from the cell which contains and expresses the DNA molecule.

6. A method for producing a trasgenic plant with modified polyfructan formation comprising:
   transforming a plant cell so as to contain and express a DNA molecule encoding a polyfructan sucrase wherein polyfructan sucrase expression leads to polyfructan sucrase activity in the vacuoles of the plant and wherein the DNA molecule is derived from *Streptococcus mutants*; and regenerating an intact whole plant from the cell which contains and expresses the DNA molecule.

7. A plant obtainable from the method of any one of claim 1, 5, or 6.

8. An intact whole transgenic plant comprising a DNA molecule encoding a bacterial polyfructan sucrase wherein the transgenic plant expresses the DNA molecule and has polyfructan sucrase expression wherein the polyfructan sucrase expression leads to polyfuctan sucrase activity in the vacuoles of the plant and has an altered amount of polyfructan sucrase activity relative to a non-transformed plant.

9. The plan of claim 8 wherein the DNA molecule is derive from *Bacillus amyloliquefaciens*.

10. The plant of claim 8 wherein the DNA molecule is derived from *Streptococcus mutans*.

* * * * *